(12) United States Patent
Vucinic et al.

(10) Patent No.: US 7,643,226 B2
(45) Date of Patent: Jan. 5, 2010

(54) MAXIMAL-APERTURE REFLECTING OBJECTIVE

(75) Inventors: Dejan Vucinic, San Diego, CA (US); Thomas M. Bartol, Carlsbad, CA (US); Terrence J. Sejnowski, Solana Beach, CA (US)

(73) Assignee: Salk Institute for Biological Studies, La Jolla, CA (US)

( * ) Notice: Subject to any disclaimer, the term of this patent is extended or adjusted under 35 U.S.C. 154(b) by 224 days.

(21) Appl. No.: 11/542,634

(22) Filed: Oct. 2, 2006

(65) Prior Publication Data
US 2007/0153368 A1    Jul. 5, 2007

Related U.S. Application Data

(60) Provisional application No. 60/723,554, filed on Oct. 3, 2005.

(51) Int. Cl.
G02B 17/00 (2006.01)
(52) U.S. Cl. .................... 359/727; 359/385; 359/364; 359/665
(58) Field of Classification Search ................ 359/364, 359/368, 727, 853, 665, 385, 389; 362/296
See application file for complete search history.

(56) References Cited

U.S. PATENT DOCUMENTS

| 4,357,075 | A | | 11/1982 | Hunter |
| 4,934,798 | A | * | 6/1990 | Bunch ..................... 359/19 |
| 5,144,496 | A | | 9/1992 | Kashima |
| 5,253,117 | A | | 10/1993 | Kashima |
| 5,291,340 | A | | 3/1994 | Kashima |
| 5,479,009 | A | * | 12/1995 | Jablonski et al. ............ 250/229 |
| 5,584,557 | A | | 12/1996 | Alexay |
| 5,699,197 | A | * | 12/1997 | Otaki ....................... 359/661 |
| 6,184,990 | B1 | | 2/2001 | Amirkhanian et al. |
| 6,185,051 | B1 | * | 2/2001 | Chen et al. ................. 359/709 |
| 6,313,467 | B1 | | 11/2001 | Shafer et al. |
| 6,356,700 | B1 | | 3/2002 | Strobl |
| 6,700,710 | B2 | | 3/2004 | Watanabe |
| 6,819,411 | B1 | | 11/2004 | Sharpe et al. |

(Continued)

FOREIGN PATENT DOCUMENTS

JP            57-187907       11/1982

(Continued)

OTHER PUBLICATIONS

Albert O. et al., "Smart microscope: an adaptive optics learning system for aberration correction in multiphoton confocal microscopy," Opt. Lett. 25:52-54 (2000).

(Continued)

*Primary Examiner*—Alessandro Amari
(74) *Attorney, Agent, or Firm*—Klarquist Sparkman, LLP

(57) ABSTRACT

Objectives and other optical assemblies include a reflective surface that is truncated at or near a focus based on a curvature of the reflective surface. A specimen is situated at or near the focus of the reflective surface, so that the reflective surface captures and collimates optical radiation emitted from the specimen. The reflective surface can be defined on an optical substrate along with a lens surface, so that an illumination flux is focused on the specimen by the lens surface, and a secondary light flux produced in response to the illumination flux is captured and collimated by the reflective surface.

16 Claims, 5 Drawing Sheets

U.S. PATENT DOCUMENTS

2003/0048740 A1* 3/2003 Nagoya et al. .......... 369/112.28
2006/0182393 A1* 8/2006 Sendur et al. ................. 385/39

FOREIGN PATENT DOCUMENTS

| JP | 1-184561 | 7/1989 |
| --- | --- | --- |
| JP | 1-184562 | 7/1989 |
| JP | 1-192747 | 8/1989 |
| JP | 1-192748 | 8/1989 |
| JP | 07-100875 | 11/1995 |
| JP | 2001-319653 | 11/2001 |

OTHER PUBLICATIONS

Beaurepaire E. et al., "Epifluorescence collection in two-photon microscopy," Applied Optics 41:5376-5382 (2002).

Denk W. et al., "Two-Photon Laser Scanning Fluorescence Microscopy," Science 248:73-76 (1990).

Feierabend M. et al., "Coherence-gated wave-front sensing in strongly scattering samples," Opt. Lett. 29:2255-2257 (2004).

Helmchen F. et al., "Deep tissue two-photon microscopy," Nature Methods 2:932-940 (2005).

Koester H. et al., "Target Cell-Dependent Normalization of Transmitter Release at Neocortical Synapses," Science 308:863-866 (2005).

Marsh P. et al., "Practical implementation of adaptive optics in multiphoton microscopy," Opt. Express 11:1123-1130 (2003).

Oheim M. et al., "Two-photon microscopy in brain tissue: parameters influencing the imaging depth," J. Neurosci. Methods 111:29-37 (2001).

Ohki K. et al., "Functional imaging with cellular resolution reveals precise micro-architecture in visual cortex," Nature 433:597-603 (2005).

Sherman L. et al., "Adaptive correction of depth-induced aberrations in multiphoton scanning microscopy using a deformable mirror," J. of Microscopy 206:65-71 (2002).

Taddeucci A. et al., "Optical properties of brain tissue," J. Biomed. Optics 1:117-123 (1996).

Theer P. et al., "Two-photon imaging to a depth of 1000 μm in living brains by use of a Ti:A$_l$2O$_3$ regenerative amplifier," Opt. Lett. 28:1022-1024 (2003).

Yaroslavsky A. N. et al., "Optical properties of selected native and coagulated human brain tissues in vitro in the visible and near infrared spectral range," Phys. Med. Biol. 47:2059-2073 (2002).

International Search Report and Written Opinion of the International Search Authority for International Application No. PCT/US06/38363, filed Oct. 2, 2006.

\* cited by examiner

MAXIMAL-APERTURE REFLECTING OBJECTIVE

CROSS-REFERENCE TO RELATED APPLICATIONS

This application claims the benefit of U.S. Provisional Application 60/723,554, filed Oct. 3, 2005 that is incorporated herein by reference.

STATEMENT OF GOVERNMENT SUPPORT

This invention was made with United States government support pursuant to grant no. MH068481 from the National Institutes of Health, and the United States government has certain rights in the invention.

TECHNICAL FIELD

The disclosure pertains to microscope objectives and microscopy methods.

BACKGROUND

Advances in microscopy have permitted increasingly sophisticated investigations of biological and other systems. In traditional microscopy, a specimen is illuminated with a broadband ("white") light source, and a magnified image of the specimen is produced. Resolution and image contrast in such systems generally depend on specimen spectral absorbance and microscope objective numerical aperture and aberrations. Microscopy can also be based on radiation produced in a specimen in response to a exposure to a suitable light flux. For example, in fluorescence microscopy, fluorescence produced in a specimen in response to a stimulating light flux is used to form a specimen image. In other examples, a specimen can emit a light flux based on a stimulating light flux via a multiphoton process. In both fluorescence microscopy and multiphoton microscopy the emitted light flux can be used to produce an image directly, or the emitted light flux can be localized by scanning the stimulating light flux across the specimen.

While microscopy-based specimen analysis based on fluorescence or multiphoton processes can provide significant specimen information, such analysis is typically hampered by inefficiencies in the fluorescence collection and multiphoton excitation processes. In some investigations, low efficiencies can be compensated for by increasing the time during which the specimen is exposed to the stimulating light flux, resulting in longer measurement times. In other examples, the stimulating light flux produces specimen changes so that increased exposures cannot be used. Therefore, improved microscopy methods and apparatus are needed.

SUMMARY

According to representative examples, optical elements comprise a concave reflector situated on an optical axis, wherein the concave reflector has a reflective surface and is truncated at a sample surface. The concave reflector is configured to direct a light flux received from a sample situated optically proximate the sample surface to a detection region. In illustrative examples, the sample surface is substantially planar and the reflective surface is defined on an exterior surface of a transparent optical substrate. In additional examples, the transparent optical substrate is configured to define a refractive optical surface that is situated on the optical axis and is configured to converge an incident light flux toward the sample surface. In other examples, a curvature of the reflective surface is aspheric such as, for example, a parabola or other conic section. In typical examples, the sample surface is situated optically proximate a focus of the reflective optical surface. In further examples, the reflective optical surface extends so as to receive a light flux over solid angles of at least about $\pi$, $1.5\pi$, $1.7\pi$, or $1.9\pi$ steradians. In other examples, the reflective optical surface includes a probe aperture that defines a probe path that couples the sample surface and the probe aperture.

According to other aspects of the technology, optical assemblies comprise a lens situated on an optical axis and configured to receive a primary light flux and converge the primary light flux toward a sample plane. A concave reflective surface is situated along the optical axis with respect to the sample plane so as to direct a secondary light flux produced in response to the primary light flux back towards the lens and along the optical axis. In some particular examples, the lens substantially occupies an exit aperture of the reflective surface and the reflective surface is configured to substantially collimate the secondary light flux.

Catadioptric objectives comprise a transparent refractive substrate having a refractive surface configured to direct an input optical beam toward a target region and a reflective surface configured to receive at least a portion of a secondary light flux propagating from the target region produced in response to the input optical beam. In some examples, the reflective surface includes a reflective coating and is a surface of rotation. According to other examples, the refractive surface is situated on an optical axis and has a positive curvature with respect to the input beam, and the reflective surface is situated on the axis and has a negative curvature with respect to the input beam. In other representative examples, the reflective surface is an aspheric surface such as a parabola or other conic section. In additional examples, a center of rotation of the refractive surface and a center of rotation of the reflective surface are situated on an optical axis. In other examples, an exit surface truncates the reflective surface and is situated substantially at a focus of the refractive surface. In other examples, an exit surface truncates the reflective surface and is situated substantially at a focus of the reflective surface.

Transparent optical substrates comprise, along an axis, an input surface defining an input aperture and configured to receive a light flux and an exit surface defining an exit aperture configured to receive the light flux from the input aperture. A reflective surface extends from the input surface to the exit surface, and the exit surface is situated optically proximate a focus of the reflective surface. In some examples, the input and exit surfaces are substantially planar, or the input surface is configured to increase a convergence of the received light flux. In other examples, an optical coating is situated at the reflective surface and is configured to enhance a reflectivity of the reflective surface.

Immersion objectives comprise a reflective surface having an input aperture configured to receive a primary light flux and an exit aperture configured to deliver the primary light flux to a sample. The reflective surface, the input aperture, and the exit aperture are situated on an optical axis, and an internal volume is defined by the input aperture, the exit aperture, and the reflective surface. An optically transmissive barrier is coupled to the reflective surface and configured to divide the internal volume into an illumination volume and an immersion volume. According to additional examples, the exit aperture is situated at a focus of the reflective surface. In still further examples, a hollow shell defines the input aperture, the exit aperture, and the reflective surface. In representative examples, the immersion volume is filled with an immersion fluid and a portion of the reflective surface that bounds the internal volume is defined on an optically transmissive substrate. In additional examples, a lens is situated at the optically transmissive barrier and configured to converge a substantially collimated light flux incident from the input aperture at the exit aperture. In still additional examples, the reflective surface includes a probe aperture in a portion of the reflective surface that defines the immersion volume, wherein the probe aperture is coupled to the immersion volume. In other typical examples, a probe aperture axis extending from the probe aperture intersects the exit aperture substantially at the optical axis, wherein an angle between the probe axis and the optical axis is less than about 60 degrees.

These and other aspects and features of the disclosed technology are described below with reference to the accompanying drawings.

DETAILED DESCRIPTION

As used in this application and in the claims, the singular forms "a," "an," and "the" include the plural forms unless the context clearly dictates otherwise. Additionally, the term "includes" means "comprises." While particular examples and applications for the disclosed embodiments are also disclosed, the described systems, methods, and apparatus should not be construed as limiting in any way. Instead, the present disclosure is directed toward all novel and nonobvious features, aspects, and equivalents of the various disclosed embodiments, alone and in various combinations and sub-combinations with one another. The disclosed systems, methods, and apparatus are not limited to any specific aspect, feature, or combination thereof, nor do the disclosed systems, methods, and apparatus require that any one or more specific advantages be present or problems be solved. In addition, the attached figures may not show the various ways in which the disclosed systems, methods, and apparatus can be used in conjunction with other systems, methods, and apparatus, and components that are well known in the art are not described in detail.

Figure 1:
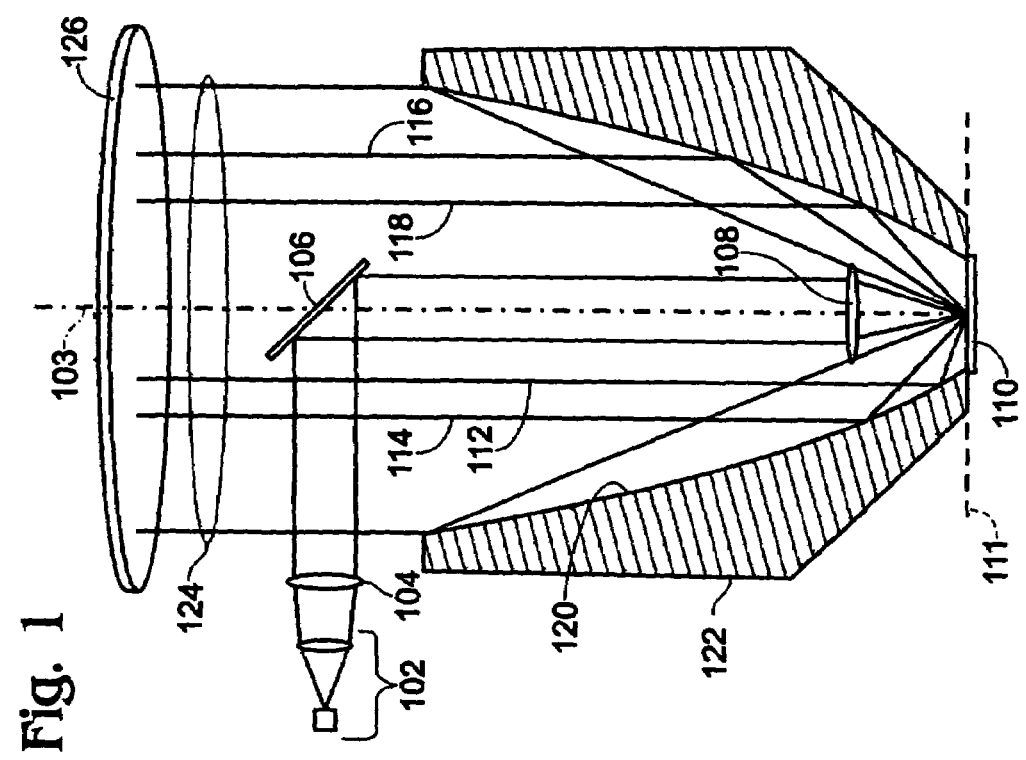
FIG. 1 is a schematic diagram of a portion of a microscopy system.

Referring to FIG. 1, a portion of a microscopy system includes an illumination source 102 configured to produce an illumination beam 104 that is directed to a specimen 110 by a reflector 106 and a lens 108 situated on an axis 103. The reflector 106 can be a front surface or rear surface reflector that includes a metallic layer, a dielectric layer, or a multilayer coating of metallic and/or dielectric layers. The layers can be selected to obtain a selected reflectance in a particular wavelength range so that the reflectance and transmittance of the reflector 106 can be configured as convenient for other wavelengths and wavelength ranges. Alternatively, the reflector 104 can be implemented as a prism, or otherwise be based on total internal reflection. As discussed below, the reflector 106 can be configured to have optical power by, for example, providing a reflective surface on a concave or convex mirror, or using a holographic element with optical power, with or without spectral selectivity.

The lens 108 is configured to converge the illumination beam on the specimen 110. In some examples, the illumination beam is substantially collimated, and the lens 108 focuses the illumination beam onto the sample 110. In other examples, the illumination beam is diverging or converging and the lens 108 is selected so that the illumination beam divergence is increased or decreased as convenient (for an incident converging illumination beam) or becomes converging (for an incident diverging illumination beam). Thus, the lens 108 can have either positive or negative optical power. In other examples, the illumination beam can be appropriately converging prior to the lens 108, and the lens 108 can be omitted or replaced with an optical element having little optical power. For example, the reflector 106 can be configured as a concave mirror that converges the illumination beam toward the sample 110 so that the lens 108 becomes unnecessary.

For convenience in illustration, the lens 108 is shown as a single lens element ("singlet"), although in many typical examples, the lens 108 is a compound lens that includes two or more optical elements such as found in, for example, microscope objectives or other compound lenses. While lenses are particularly convenient, in additional examples, a curved mirror or combination of mirrors and lenses can be used to focus or direct the illumination beam 104. For example, reflecting microscope objectives based on the Schwarzchild objective or on a Cassegrain reflector configuration can be used. The Schwarzchild objective is configured to convert one image plane into another image plane, while Cassegrain reflector configurations have infinite conjugates. Thus, some adjustment is preferred to accommodate the infinite conjugate to image plane focusing applied to the illumination beam 104.

The illumination beam 104 is generally selected to produce emitted radiation at the specimen 110 in association with an intended measurement or specimen characterization. For example, in a fluorescence measurement, a wavelength range of the illumination beam is selected to induce fluorescence in the specimen 110 or in fluorophores provided by or associated with the specimen 110. Alternatively, for non-fluorescence based valuations based on, for example, light scattering, a wavelength range of the illumination beam can be selected to enhance light scattering. In multiphoton measurements, illumination beam optical power can be selected as well. To enhance production of multiphoton-based radiation, peak optical powers can be selected. For convenience in describing embodiments of the technology, optical radiation emitted by or otherwise emanating from the specimen 110 is referred to as exiting radiation or "secondary radiation." The illumination beam that produces this secondary radiation can be referred to as "primary" radiation." In some examples, this exiting radiation is wavelength shifted as a result of fluorescence or a multiphoton process, and such exiting radiation is accordingly referred to as wavelength shifted. In some applications, primary radiation is generally in a portion of the electromagnetic spectrum from about 200 nm to about 2000 nm, but primary radiation can be at other wavelengths as well. For example, primary radiation can be at soft x-ray wavelengths, extreme ultraviolet wavelengths, or at infrared or far infrared wavelengths. Wavelengths between at least about 1 nm and 20 μm can be used, and all reflecting designs permit the use of wavelengths at which refractive materials are unsuitable. In reflective systems, surface reflectivity can be enhanced with multilayer or other coatings.

As shown in FIG. 1, the exiting radiation propagating along representative rays 112, 114, 116, 118 is incident to a reflective surface 120 of a reflector assembly 122. The surface 120 is configured to direct the exiting radiation along the axis 103 and to converge, collimate, or at least partially converge or collimate the exiting radiation to form an exit beam 124. The exit beam 124 is received by a lens 126 and further converged, diverged, focused or otherwise processed for delivery to a detector or detector array, or additional processing optical elements.

The reflective surface 120 can be conveniently selected as a parabolic surface or to substantially approximate a parabolic surface. For such a surface, the reflector assembly can be truncated at a truncation plane 111 so that the specimen 110 (or a selected region of interest in the specimen) can be situated substantially at a focus of the parabolic surface. In this way, the exiting radiation is substantially collimated by the reflective surface 120. In addition, situating the specimen 110 at or near a focus permits the reflective surface 120 to capture exiting radiation over a large solid angle. As shown in the schematic diagram of FIG. 1, the lens 108 and the reflector 106 are the only potential limitations on collection of exiting radiation on an illumination beam side of the specimen 110. The reflector 106 can be configured to substantially transmit exiting radiation by using, for example, a multilayer dielectric reflective layer or a holographic reflector so that reflection at the reflector 106 is based on wavelength or angle of incidence or both. The lens 108 can be configured to substantially collimate a portion of the exiting radiation incident to the lens 108, so that, in combination, the reflective surface 120 and the lens 108 direct exiting radiation from substantially all of the solid angle on the illumination beam side of the specimen 110 into the exit beam 124.

The reflective surface 120 can be conveniently selected to be parabolic, elliptical, hyperbolic, spherical, or a generalized aspheric surface. The reflective surface 120 need not be rotationally symmetric, and cylindrical surfaces including surfaces having different curvatures along different axes can be used, wherein the curvatures can be selected to be parabolic, elliptic, hyperbolic, spherical, or otherwise aspheric.

In some examples, imaging of the specimen 110 is achieved by scanning the illumination light flux across the specimen 110. Exiting light flux associated with some or all specimen locations can be collected and used to provide a specimen image. Typically a laser or other collimated light source provides the illumination light flux, and varying a tilt angle of the reflector 106 can scan the converging or focused beam across the specimen, but other scanning methods can also be used. For example, acousto-optic scanners can be used. In applications in which the illumination light flux is scanned, image resolution can be based on the detected exiting radiation from some or all locations, so that imaging requirements imposed on the reflective surface 120 can be modest, and the reflective surface 120 can exhibit significant aberrations without adversely affecting image resolution.

Figure 2:
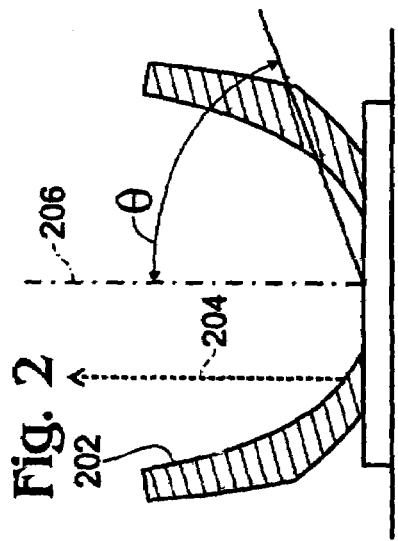
FIGS. 2-3 are schematic diagrams illustrating light collection solid angles associated with microscopy systems such as illustrated in FIG. 1.
Figure 3:
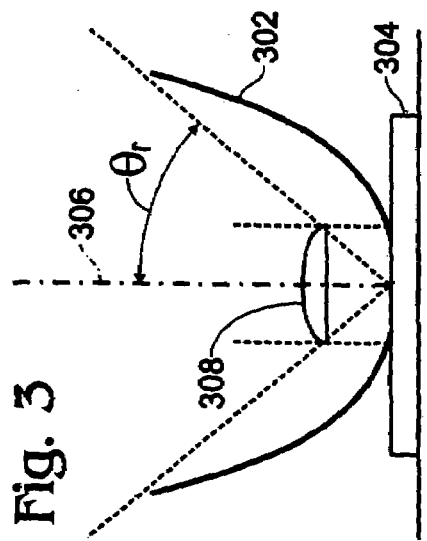

FIGS. 2-3 are schematic diagrams illustrating light gathering apertures available in representative examples. Referring to FIG. 2, a reflective surface 202 is configured to receive exiting light propagating along, for example, a representative ray 204 such that, after reflection, the ray 204 is substantially parallel to an axis 206. In FIG. 2, the reflective surface 202 is configured to substantially collimate the exiting radiation but, as noted above, different collimation configurations can be selected. As is apparent from FIG. 2, exiting radiation is collected and directed by the reflective surface in cooperation with a lens such as the lens 108 within a cone of half angle θ. The solid angle subtended by such a cone is $2\pi[1-\cos(\theta/2)]$ so substantially all exiting radiation is captured. In representative examples, the half angle θ is at least about 60 degrees, 75 degrees, 80 degrees, or 85 degrees.

Referring to FIG. 3, a reflective surface 302 is configured to collimate an exiting light flux received from a specimen 304 so as to propagate along an axis 306. A lens 308 that is typically provided to direct an illumination flux to the specimen 304 receives a portion of the exiting radiation that is directed into a cone of angle $\theta_r$. Such radiation does not intersect the reflective surface 302. The lens 308 is configured to collimate or substantially collimate this portion of the exiting radiation, so that the lens 308 is not associated with any appreciable reduction in exiting radiation exiting along the axis 306.

Figure 4:
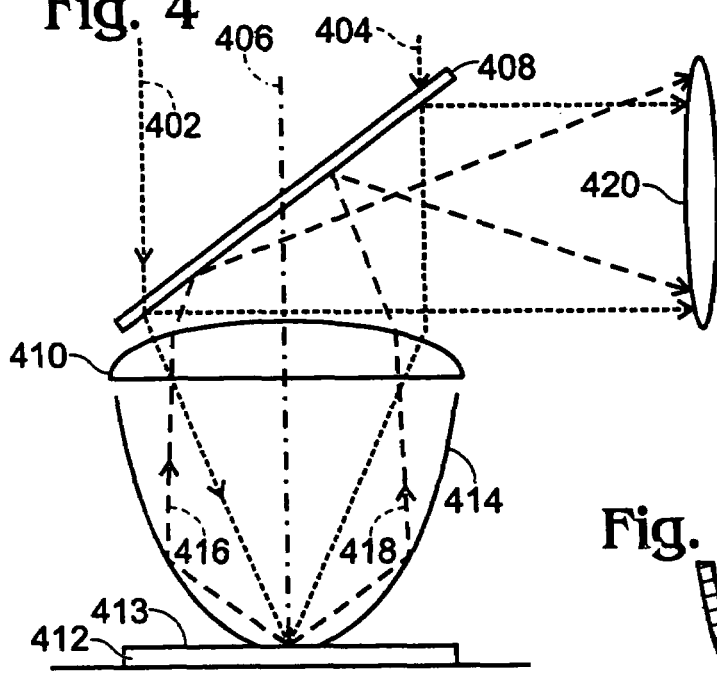
FIG. 4 is a schematic diagram of another example of a microscopy system.

With reference to FIG. 4, an illumination light flux shown as rays 402, 404 propagates along an axis 406 through a beamsplitter 408 and to a focusing lens 410. The beamsplitter 408 is configured to substantially transmit the illumination light flux and reflect an exiting light flux, such as, for example, a wavelength shifted light flux associated with, for example, fluorescence or a multiphoton process. The illumination light flux is focused or otherwise converged by the lens 410 and is incident to a target 412. A specimen of interest can be conveniently situated on or near a surface 413 of the target 412. Exiting radiation (such as, for example, fluorescence) is reflected by a reflective surface 414 and propagates along example rays 416, 418 to the lens 410. The lens 410 can increase exiting radiation beam convergence, and the exiting radiation can be reflected by the beamsplitter 408 to a detector 420 or additional optics for further processing. In the example of FIG. 4, the lens 410 is configured to direct an illumination light flux to the target 412 and to direct (in cooperation with the reflective surface 414) the exiting radiation to the detector 420.

Figure 6:
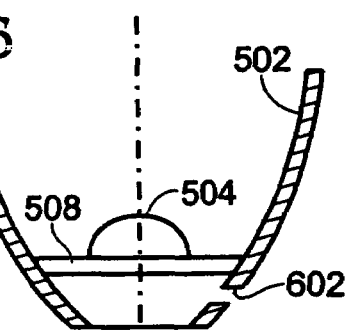
FIG. 6 is a schematic diagram of a reflector that includes a probe aperture.
Figure 5:
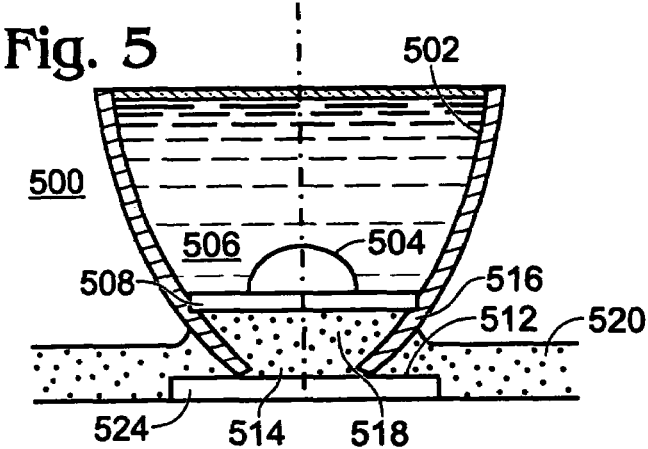
FIG. 5 is a schematic diagram of a reflector having an interior volume that has a portion that is filled with an immersion liquid.

With reference to FIG. 5, a reflective objective 500 includes a reflective surface 502 and a lens 504. An interior volume 506 defined by the reflective surface 502 and a window 508 can be filled with a high refractive index material such as an immersion oil (n=1.56) or water, and the lens 504 can be attached to or otherwise situated in the volume 506 by the window 508. The reflective surface 502 terminates at a sample plane 512, and includes an aperture 514 that permits fluid entry into a volume 518. A portion 516 of the reflective surface 502 situated between the window 508 and the sample plane 512 can be defined as a continuation of a portion of the reflective surface defining the volume 506, but in some examples, this portion can be configured for mechanical support, to provide a suitable spacing of the lens 504, the sample plane 512, and a focal point or focal plane of the reflective surface 502, or otherwise configured. In this alternative, any exiting radiation from the sample plane 512 incident to the reflector portion 516 may be lost for further processing. As shown in FIG. 5, perfusion fluid 520 fills the volume 518 and at least partially covers a specimen support 524. FIG. 6 is a schematic diagram of a reflective objective similar to that of FIG. 5 but that includes an aperture 602 configured to receive an electrode, a patch pipette, or other specimen probe to permit additional specimen manipulation, stimulation, or measurement.

Figure 7:
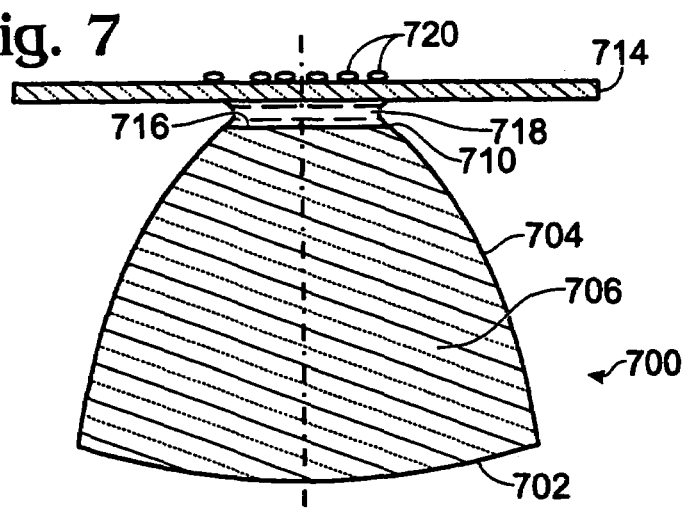
FIG. 7 is a schematic diagram of an objective defined by a transparent substrate.

With reference to FIG. 7, an objective 700 that is of unitary one-piece construction includes a reflective surface 704 and a lens surface 702 that are defined in a single optically transmission substrate 706. Curvature of the reflective surface 704 is defined by the substrate 706, and a dielectric or metallic coating or a holographic layer can be provided to enhance or spectrally configure reflectance. The substrate 706 is truncated at a sample plane 710, and a specimen support 714 is optically contacted to a termination 716 of the substrate 706 with a liquid 718 such as an immersion oil, water, or other liquid. Alternatively, an air gap can be provided. As shown in FIG. 7, representative sample portions 720 such as cells are situated on a surface of the specimen support 714. In this example, a single substrate provides convergence of an illumination light flux, and collection/convergence of exiting radiation.

Figure 8:
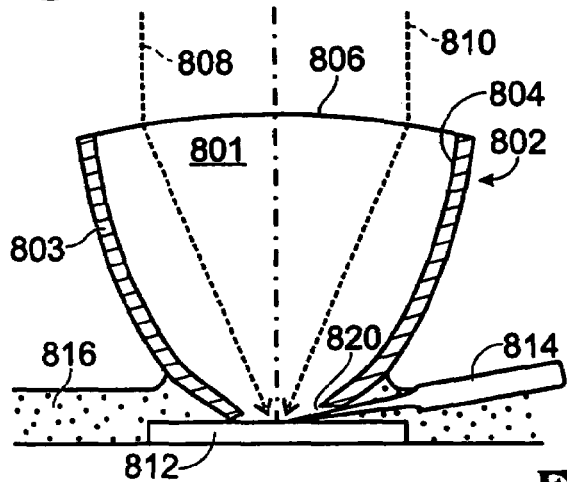
FIG. 8 is a schematic diagram of an objective and an electrode situated for specimen analysis.

Referring to FIG. 8, a unitary objective 802 includes a transmissive substrate 801 having a reflective surface 804 and a refractive surface 806. The refractive surface 806 is configured to direct an illumination flux incident along representative rays 808, 810 to a specimen support 812, such as a microscope slide or cover slip, and, in cooperation with the reflective surface 806, gathers and converges or otherwise delivers exiting radiation to a detector or additional optical elements for processing. A coating can be provided to enhance reflectivity. The substrate 801 is truncated at the specimen support based on a curvature of the reflective surface 806 so that exiting radiation is collected, collimated, or converged as needed for a particular application. Typically, truncation is at or near a focus of the reflective surface 806. The substrate 801 also includes a relief zone 820 or aperture configured to permit access to the specimen support 812 by an electrode 814 or other probe.

Figure 10:
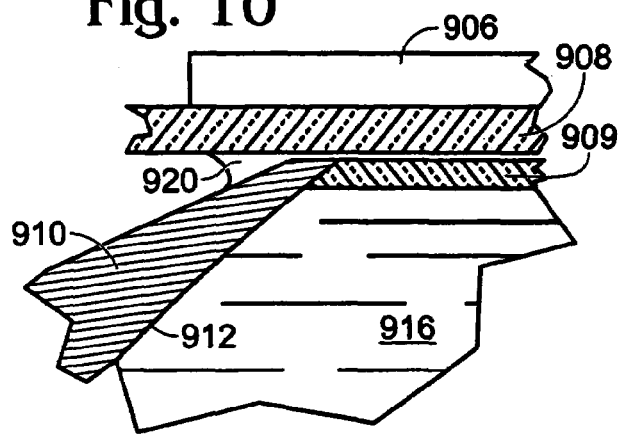
FIG. 10 is a schematic diagram of a portion of the microscope system illustrated in FIG. 9.
Figure 9:
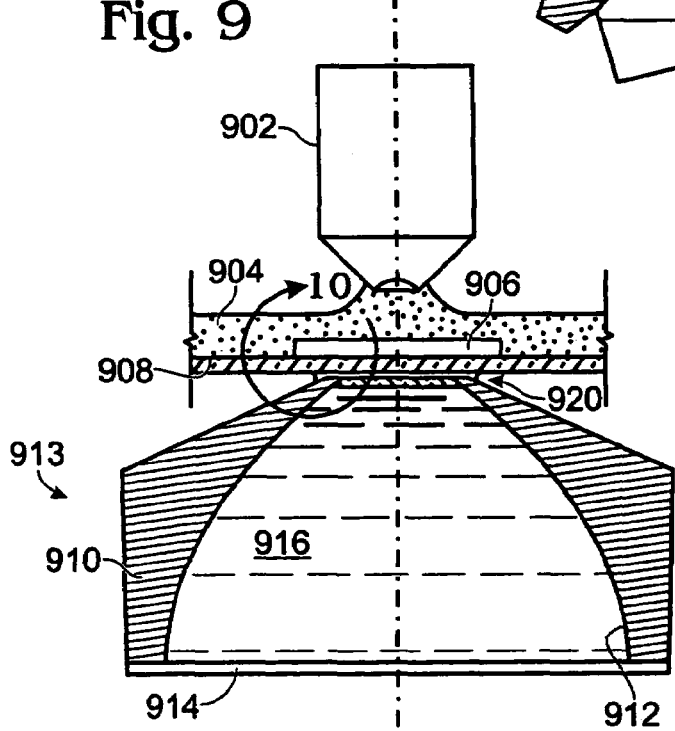
FIG. 9 is a schematic diagram of a microscope system that includes a truncated reflector situated so that a sample is situated at or near a focus of a reflective surface of the truncated reflector.

FIGS. 9-10 illustrate a representative example in which a truncated reflective surface 912 of a reflective light collector 913 and a conventional microscope objective 902 are configured so that an illumination light flux and an exiting light flux are situated on opposite sides of a specimen. The microscope objective 902 contacts an perfusion fluid layer 904 that covers or partially covers a specimen 904 such as a tissue layer that is supported by, for example, a chamber wall or microscope slide 908. An interior volume 916, defined by the reflective surface 912, an entrance window 909, and an exit window 914 can be filled with an immersion oil or other material. In this example, the light collector 913 can be substituted for a conventional microscope condenser. The entrance window 909 and the microscope slide 908 can be optically contacted with a layer 920 of immersion oil or other material.

Figure 11:
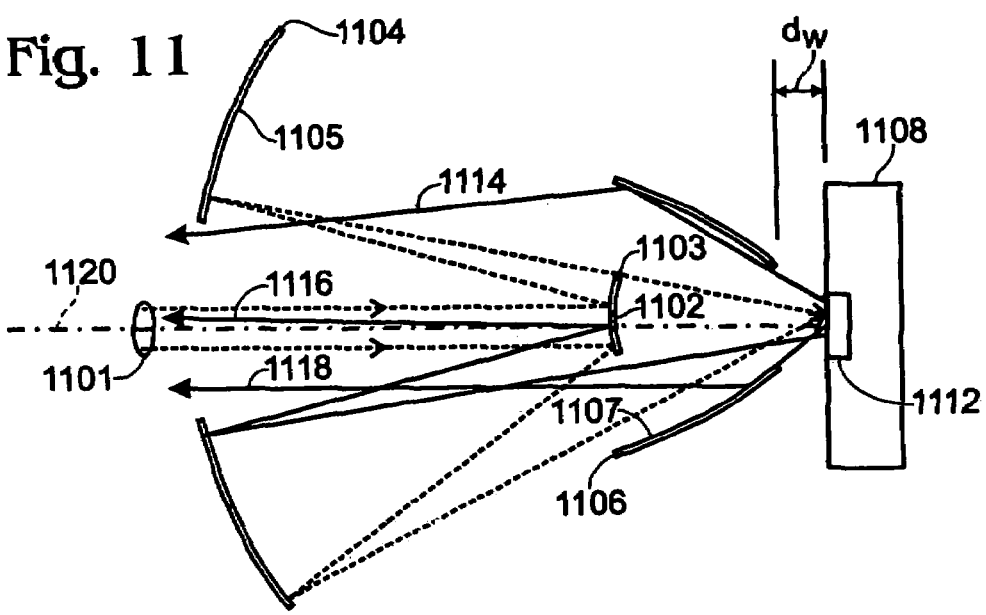
FIG. 11 is a schematic diagram of a reflective optical system that includes an objective based on a Cassegrain configuration that is adapted to direct an incident light flux to an image plane for illumination of a specimen.

FIG. 11 illustrates an all-reflecting optical system. Reflective surfaces 1103, 1105 or respective reflectors 1102, 1104 receive an incident light flux 1101 and direct the incident light flux 1101 to a region of interest 1112 on, for example, a tissue specimen 1108. Curvatures of the reflective surfaces 1103, 1105 can be selected so that the incident light flux 1101 can be focused to a nearly diffraction-limited spot at the specimen 1108. A non-imaging reflector 1106 receives light scattered or emitted in response to the illumination flux at a reflective surface 1107, and directs this light to a detector or other optical system (not shown in FIG. 11). For example, scattered or emitted light directed along representative ray directions 1114, 1116, 1118 can be focused, reflected, or otherwise processed for delivery to a detector or other optical system.

As shown in FIG. 11, the reflectors 1102, 1104, 1106 are rotationally symmetric about an optical axis 1120, but in other examples, asymmetric, tilted, or other surfaces can be used. Reflective surfaces can be conveniently provided by metallic, dielectric, holographic, or other coatings. In some examples, one or more spectrally selective coatings can be used. The reflective surfaces 1103, 1105, 1107 can be selected to be substantially spherical, elliptical, parabolic, or hyperbolic, or can be aspherical and described based on a polynomial expansion.

Representative reflector specifications are provided in the table below. As used in this table, a mirror surface can be described as a surface sag X as a function of surface height Y (typically distance from an axis) such that $$X = \frac{cY^2}{1 + \sqrt{[1 - c^2 Y^2 (1 - e^2)]}} + a^4 Y^4 + a^6 Y^6 + a^8 Y^8 + a^{10} Y^{10},$$

wherein c is a spherical curvature, e is an eccentricity, and $a_4$, $a_6$ $a_8$ $a_{10}$ are aspheric coefficients. For convenience, the term $-e^2$ is referred to as the conic constant, and abbreviated CC herein. This representation of a surface is described in detail in, for example, Rudolf Kingslake, *Lens Design Fundamentals*, Academic Press, New York (1978) that is incorporated herein by reference. A mirror specification d represents axial distance between surfaces. For example, optical surface separation along an axis.

Specifications $r_{min}$, and $r_{max}$ represent apertures of sufficient size to collect and deliver selected portions of an illumination light flux or a light flux emitted or scattered in response. For example, the reflective surface 1103 extends from an optical axis OA to a radial distance of 2.9 mm. The reflective surface 1105 has a central aperture for light entrance and exit of radius 10.5 mm and an overall radius of 42 mm. These dimensions are dependent on numerical aperture, and different values can be used.

Optical Specifications for FIG. 11. (All dimensions in mm.)

| Surf. | c | CC | $a_4$ | $a_6$ | $a_8$ | $a_{10}$ | d | $r_{min}$ | $r_{max}$ |
|---|---|---|---|---|---|---|---|---|---|
| 1103 | 6.5 | 0.876 | $-2.857 \cdot 10^{-4}$ | $-7.594 \cdot 10^{-6}$ | $-2.241 \cdot 10^{-7}$ | $-1.442 \cdot 10^{-8}$ | $-45$ | | 2.9 |
| 1105 | 54.648 | $1.3 \cdot 10^{-4}$ | $-1.828 \cdot 10^{-9}$ | $-3.967 \cdot 10^{-13}$ | $1.678 \cdot 10^{-17}$ | $-6.175 \cdot 10^{-20}$ | 66.0483 | 10.5 | 42.0 |
| 1107 | $-5.988$ | $-0.93$ | | | | | $-3.0483$ | 6.9 | 13.5 |

As summarized in the table above, the reflective surface 1107 is almost parabolic with a conic constant of −0.93 (a parabola has a conic constant of −1). The configuration of FIG. 11 is all-reflective and introduces no additional temporal dispersion so that it is particularly adapted for use with femtosecond or other short pulse illumination. In addition, as shown in FIG. 11, the reflector 1106 is displaced along the axis 1120 for the specimen by a working distance $d_w$ that is typically conveniently selected to be about 1 mm. The effective (immersed) numerical aperture of the illumination system (reflectors 1102, 1104) is about 0.86 (0.65 in air) at a magnification of about 30, and a typical field of view has a diameter of about 200 µm.

In typical applications, a scattered or secondary light flux appears to originate at a location different from its true origin. As a result, superior collection efficiency can be achieved by a relative displacement of the reflectors 1102, 1104 and the reflector 1106 along the axis 1120. Typically, the reflector 1106 can be configured to receive a light flux that appears to originate within a region extending about one scattering length deep into the specimen 1108. In this configuration, a focus for the illumination light flux can be located further within the specimen than an apparent origin of the secondary radiation, and an effective focus of the reflector 1106 can be displaced from that of the reflectors 1102, 1104. However, with a specimen that is a thin turbid slab with a reflector provided on an exit surface of the slab, opposite focal displacements can be used (i.e., the source of secondary radiation is deeper in the specimen than a reflected focus of the illumination reflectors). Thus, collection efficiencies can be improved with displacement of the effective foci of illumination and collection optics.

Figure 12:
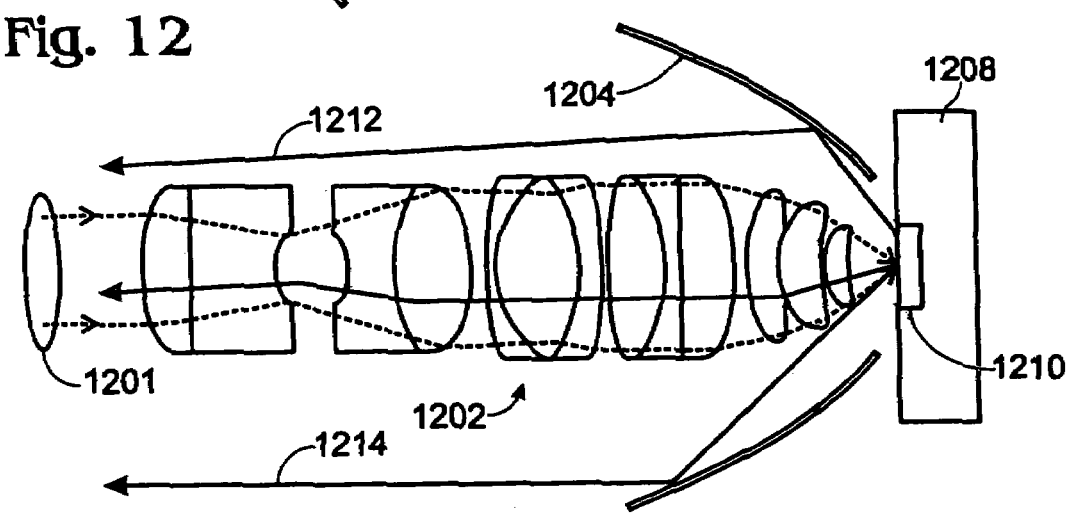
FIG. 12 is a schematic diagram that includes a microscope objective for directing an illumination beam to a target, and a reflector configured to direct light from the target to a detector.

FIG. 12 illustrates a refracting objective 1202 configured to deliver an illumination flux 1201 to a region of interest (ROI) 1210 of a tissue specimen 1208. Scattered or emitted light from the ROI 1210 directed along, for example, representative ray directions 1212, 1214, is reflected by a non-imaging reflector 1204 for delivery to a detector (not shown in FIG. 12).

Figure 13:
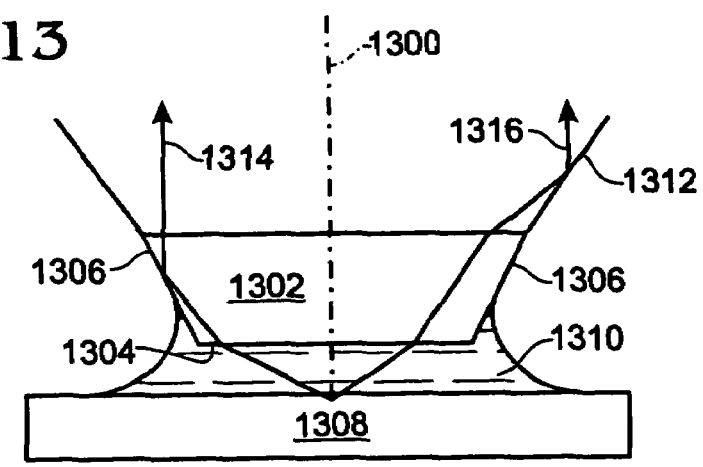
FIG. 13 is a schematic diagram that illustrates a glass termination configured to direct a light flux emitted or scattered by a target to a detector.

FIG. 13 illustrates an arrangement that can provide increased collection of a scattered or emitted light flux such as that produced by, for example, epifluorescence. A collection reflector 1312 and an immersion element 1302 are situated along an axis 1300 and are configured to receive a light flux emitted by or scattered from a specimen 1308. The immersion element has a surface 1304 that is adapted to contact an immersion fluid layer 1310 that is situated on a surface of the specimen 1308. The immersion fluid layer 1310 can be an immersion oil layer or other liquid layer, or the immersion fluid can be omitted and an air gap provided between the surface 1304 and the specimen 1308, but light collection efficiency is generally substantially improved using an immersion fluid layer. The immersion element 1302 also includes a side surface 1306 that is configured to have a relatively high reflectivity for a light flux received from the specimen 1308. High reflectivity can be provided by total internal reflection or with a dielectric, metallic, or other coating. Such coatings can be broadband coatings, or can be selected to provide a high reflectance only at wavelengths associated with, for example, epifluorescence.

The immersion element 1302 is conveniently made of glass, fused silica, or other material that is substantially transparent in a region of interest. In a typical example, the immersion element 1302 is rotationally symmetric about the axis 1300. The side surface 1306 can be configured to correspond to sides of a cone so that as projected into a plane containing the axis 1300, the side surface 1306 appears as a straight line. The side surface 1306 can also be selected to correspond to a portion of a spherical, elliptical, parabolic or other aspheric surface. In other examples, the immersion element 1302 can include one or more edge facets instead of a single continuous side surface as illustrated in FIG. 13.

As shown in FIG. 13, a portion of a light flux from the specimen 1308 that is directed along a ray direction 1316 is transmitted by the immersion element 1302 and reflected by the collection reflector 1312 to a detector or other optical system (not shown in FIG. 13). A portion of the light flux propagating along a ray direction 1314 is reflected by the side surface 1306 and can be directed to a detector without reflection by the collection reflector 1312.

Figure 14:
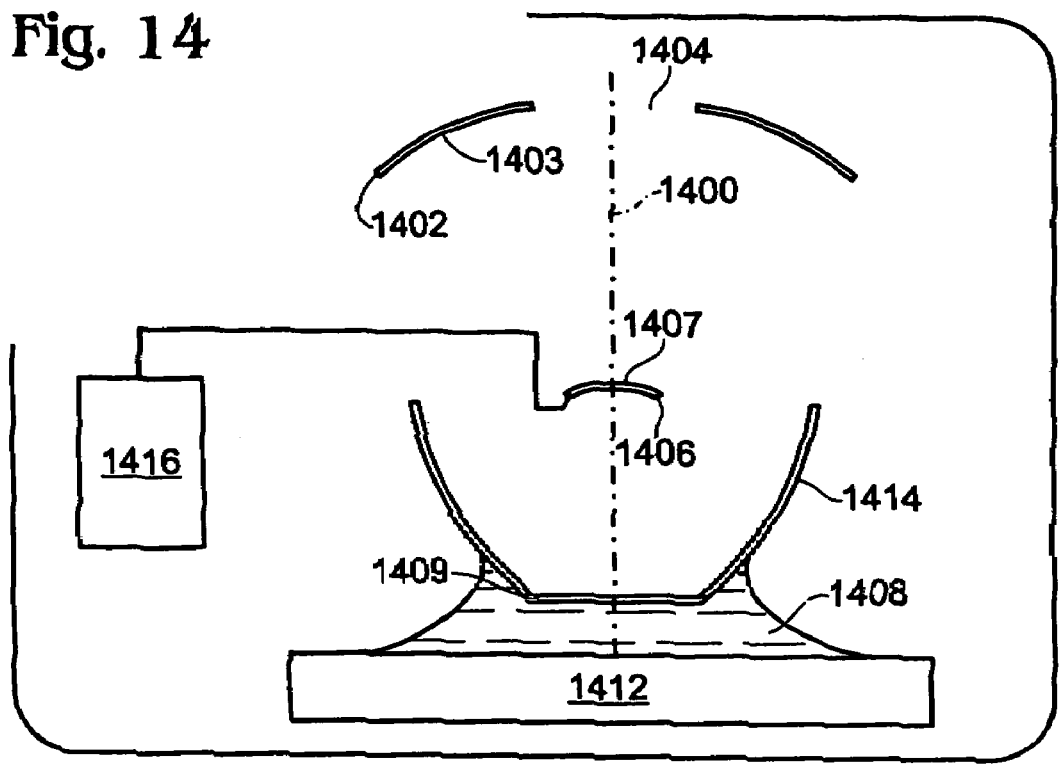
FIG. 14 is a schematic diagram of an optical system that includes a deformable mirror.

FIG. 14 illustrates a representative optical system that includes reflectors 1402, 1406 that are configured to deliver an illumination flux along an axis 1400. An incident light flux propagating along the axis 1400 is transmitted by an aperture 1404 to a deformable reflective surface 1407 of the reflector 1406. The deformable reflective surface 1407 directs the light flux to a reflective surface 1403 of the reflector 1402 that reflects the light flux to a specimen 1412 through a window 1409 and an immersion fluid 1408. Fluorescence or other emitted or scattered light from the specimen 1412 can be directed by a reflector 1414 to another optical system or a detector. The window 1409 can be conveniently secured to the reflector 1414.

In many practical examples, the incident light flux propagates into the specimen 1412 in order to produce fluorescence or other scattered or emitted light flux that is to be used for specimen investigation. The specimen 1412 can introduce significant optical aberrations into the incident light flux. Such aberrations can be reduced or eliminated by adjusting a curvature of the deformable reflective layer 1407 based on an input from a control system 1416, or otherwise adapt a curvature or phase of an illumination flux.

Figure 15:
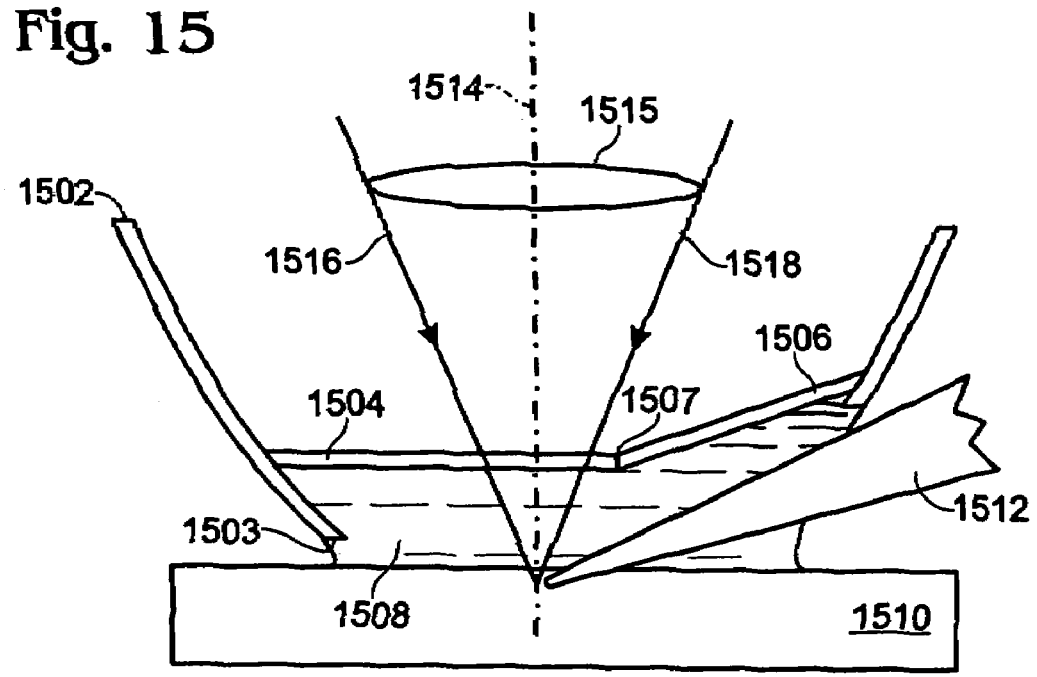
FIG. 15 is a schematic diagram of a collection optical system that includes first and a second windows configured to probe access to a specimen.

An alternative termination of a fluorescence collection reflector 1502 is illustrated in FIG. 15. A first window 1504 and a second window 1506 are secured to a specimen side 1503 of the collection reflector 1502 and are configured to contact a immersion or perfusion fluid layer situated on a specimen 1510. The first window 1504 and the second window 1506 join at an intersection 1507, and the second window 1506 is oriented to provide access to the specimen 1510 by, for example, a patch pipette 1512. In addition, a portion of the reflector 1502 is removed to permit access to the specimen.

A clear aperture of the first window 1504 can be selected for transmission of marginal rays 1516, 1518 associated with an illumination light flux. If the intersection 1507 is positioned in this way, the illumination light flux is substantially transmitted by the first window 1504. In other examples, portions of the illumination light flux can be transmitted by both the first window 1504 and the second window 1506.

The preceding examples are representative of some principles of the disclosed technology. In some examples, incident and exiting optical beams are referred to as being focused by one or more optical elements. While in some examples, a beam focus can be associated with a position at which an at least approximately minimum beam diameter is established, in other examples a beam focus more broadly encompasses a position or plane at which a beam is sufficiently converged to have a selected beam diameter, not necessarily a minimum beam diameter. Converging optical elements such as lenses having positive powers generally have an associated focus or focal point at which a collimated beam is focused. A beam propagating parallel to an axis of such an element is generally converged to a focal point. Typically a focal point is an on-axis point in an associated focal plane. In some examples, optical elements can lack well defined focal planes due to, for example, focusing aberrations, but a plane of "best" focus can be defined, and such a plane may or may not include the on-axis focal point.

In the examples, exiting radiation can be collected over substantial solid angles, ranging up to solid angles that are approximately $2\pi$ steradians. In examples in which front side and back side light collection is practical, collection angles can approach $4\pi$ steradians by placing collection optics on both sides of a specimen. It will be apparent that these examples can be rearranged without departing from the disclosed principles. Accordingly, the examples are not to be taken as limiting in any way. We claim all that is encompassed both literally and by equivalents to the appended claims.

We claim:

1. An optical element, comprising a concave reflector situated on an optical axis, the concave reflector having a reflective surface and being truncated at a sample surface, wherein the concave reflector is configured to direct a light flux received from a sample situated optically proximate the sample surface to a detection region, the concave reflector further having a probe aperture displaced from the optical axis and situated so as to provide access to the sample surface through the reflective surface.

2. An immersion objective, comprising:
a reflective surface having an input aperture configured to receive a primary light flux and an exit aperture configured to deliver the primary light flux to a sample, wherein the reflective surface, the input aperture, and the exit aperture are situated on an optical axis, and an internal volume is defined by the input aperture, the exit aperture, and the reflective surface, and wherein the reflective surface is truncated at a sample surface so as to define the exit aperture, and the reflective surface is configured to direct a light flux received from a sample situated optically proximate the sample surface to a detection region; and
an optically transmissive barrier coupled to the reflective surface and configured to divide the internal volume into an illumination volume and an immersion volume.

3. The immersion objective of claim 2, wherein a curvature of the reflective surface is aspheric.

4. The immersion objective of claim 3, wherein the curvature of the reflective surface corresponds to a conic section.

5. The immersion objective of claim 4, wherein the conic section is a parabola.

6. The immersion objective of claim 2, wherein the sample surface is situated optically proximate a focus of the reflective optical surface.

7. The immersion objective of claim 2, wherein the reflective surface extends so as to receive a light flux from the sample surface in a solid angle of at least about $1.5\pi$ steradians.

8. The immersion objective of claim 2, wherein the reflective surface includes a probe aperture that defines a probe path that couples the sample surface and the probe aperture.

9. The immersion objective of claim 2, wherein the exit aperture is situated at a focus of the reflective surface.

10. The immersion objective of claim 2, further comprising a hollow shell that defines the input aperture, the exit aperture, and the reflective surface.

11. The immersion objective of claim 2, wherein the immersion volume is filled with an immersion fluid.

12. The immersion objective of claim 2, wherein a portion of the reflective surface that bounds the internal volume is defined on an optically transmissive substrate.

13. The immersion objective of claim 2, further comprising a lens situated at the optically transmissive barrier and configured to converge a substantially collimated light flux incident from the input aperture at the exit aperture.

14. The immersion objective of claim 2, wherein the reflective surface includes a probe aperture in a portion of the reflective surface that defines the immersion volume, wherein the probe aperture is coupled to the immersion volume.

15. The immersion objective of claim 14, wherein a probe aperture axis that extends from the probe aperture intersects the exit aperture substantially at the optical axis, wherein an angle between the probe axis and the optical axis is less than about 60 degrees.

16. The immersion objective of claim 2, wherein the sample surface is substantially planar.

* * * * *